United States Patent [19]
Grage et al.

[11] Patent Number: 5,968,765
[45] Date of Patent: Oct. 19, 1999

[54] OPAQUE REACTION MATRIX FOR THE ANALYSIS OF THE WHOLE BLOOD

[75] Inventors: Henry M. Grage, Danville; Joel S. Douglas, Santa Clara; Pat S. Lee, Menlo Park, all of Calif.

[73] Assignee: Mercury Diagnostics, Inc., Scotts Valley, Calif.

[21] Appl. No.: 08/961,942

[22] Filed: Oct. 31, 1997

Related U.S. Application Data

[60] Provisional application No. 60/030,767, Nov. 8, 1996.

[51] Int. Cl.[6] .............................. C12Q 1/26; C12Q 1/54; C12Q 1/00
[52] U.S. Cl. .................................. 435/25; 435/14; 435/1; 435/4; 435/970; 435/968
[58] Field of Search .................................. 435/25, 14, 2, 435/4, 970, 968

[56] References Cited

U.S. PATENT DOCUMENTS

| | | | |
|---|---|---|---|
| 4,340,479 | 7/1982 | Pall | 435/25 |
| 4,477,575 | 10/1984 | Vogel et al. | 435/4 |
| 4,629,563 | 12/1986 | Wrasidlo | 435/25 |
| 4,645,744 | 2/1987 | Charlton et al. | 435/25 |
| 4,774,039 | 9/1988 | Wrasidlo | 435/25 |
| 4,774,192 | 9/1988 | Terminiello et al. | 435/970 |
| 4,781,890 | 11/1988 | Arai et al. | 435/25 |
| 4,786,595 | 11/1988 | Arai et al. | 435/25 |
| 4,895,704 | 1/1990 | Arai et al. | 435/25 |
| 4,992,178 | 2/1991 | Chaufer et al. | 435/25 |
| 4,994,238 | 2/1991 | Daffern et al. | 435/25 |
| 5,049,487 | 9/1991 | Phillips et al. | 435/25 |
| 5,124,128 | 6/1992 | Hildenbrand et al. | 435/25 |
| 5,186,843 | 2/1993 | Baumgardner et al. | 435/25 |
| 5,306,623 | 4/1994 | Kiser et al. | 435/25 |
| 5,418,142 | 5/1995 | Kiser et al. | 435/25 |
| 5,456,835 | 10/1995 | Castino et al. | 435/25 |
| 5,627,075 | 5/1997 | Bateson | 435/4 |

FOREIGN PATENT DOCUMENTS

| | | |
|---|---|---|
| 0207392A2 | 1/1987 | European Pat. Off. . |
| 0524596A1 | 1/1993 | European Pat. Off. . |
| 3407359 | 8/1985 | Germany . |
| WO 97/38126 | 10/1997 | WIPO . |

*Primary Examiner*—Louise N. Leary
*Attorney, Agent, or Firm*—Burns, Doane, Swecker & Mathis, LLP

[57] ABSTRACT

A test strip for use in determining the presence or concentration of an analyte in whole blood is disclosed. The test strip is a porous membrane having disposed thereon (a) a separating agent capable of separating from whole blood, red blood cells and a fluid component substantially free of red blood cells; (b) an indicating reagent system capable of indicating the presence or concentration of an analyte in the fluid component by producing a spectrophotometric change upon contact with the fluid component; and (c) an opaque filler capable of reducing spectrophotometric interference caused by the presence of the red blood cells. Also disclosed are methods of testing whole blood for the presence or concentration of an analyte using the test strip.

32 Claims, 3 Drawing Sheets

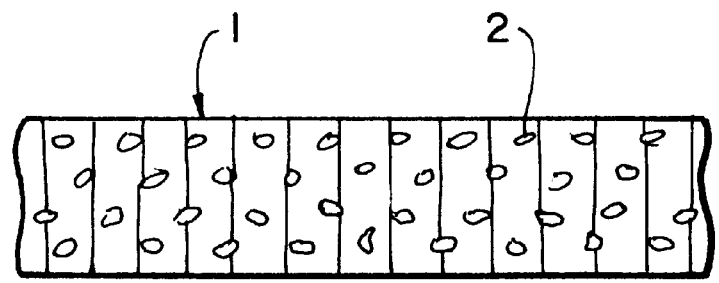
FIG_1A
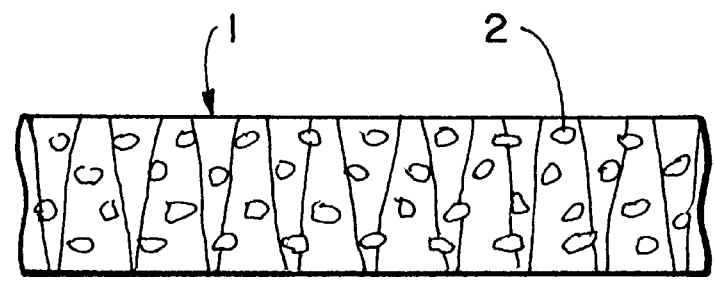
FIG_1B
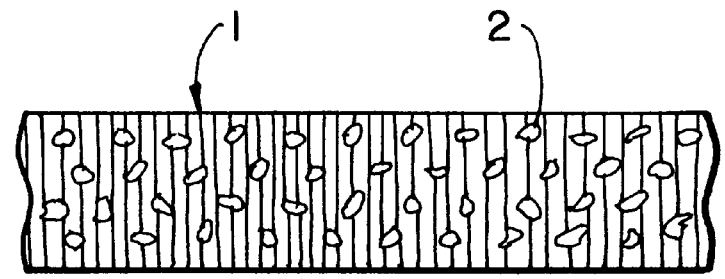
FIG_1C

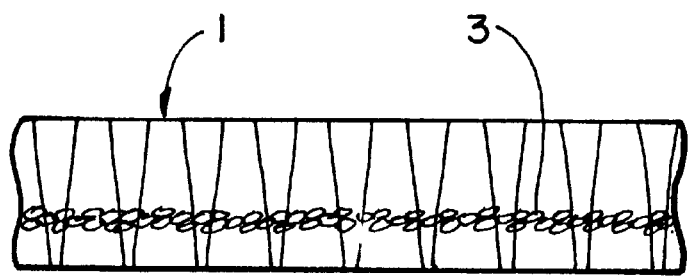
FIG_2
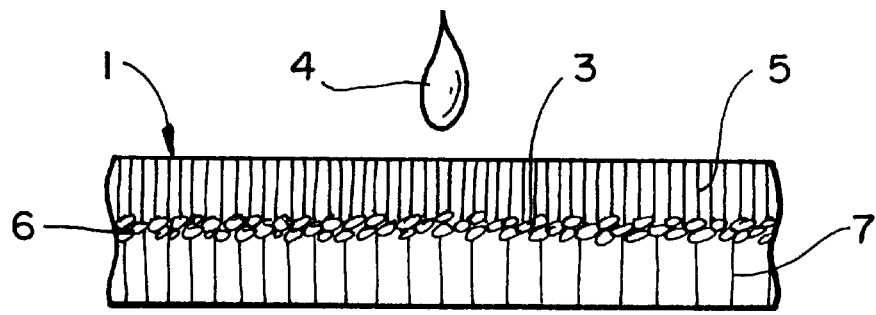
FIG_3A
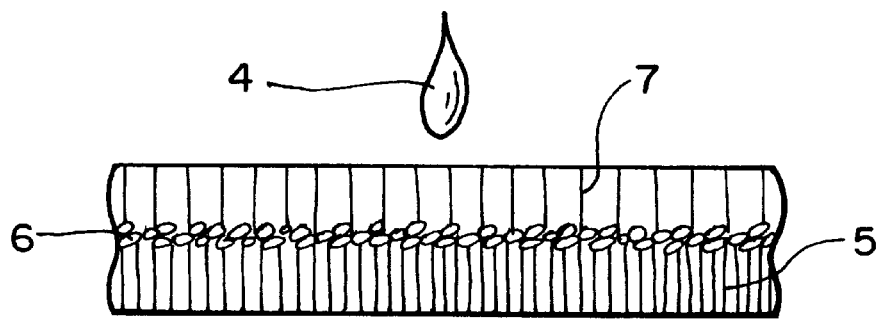
FIG_3B

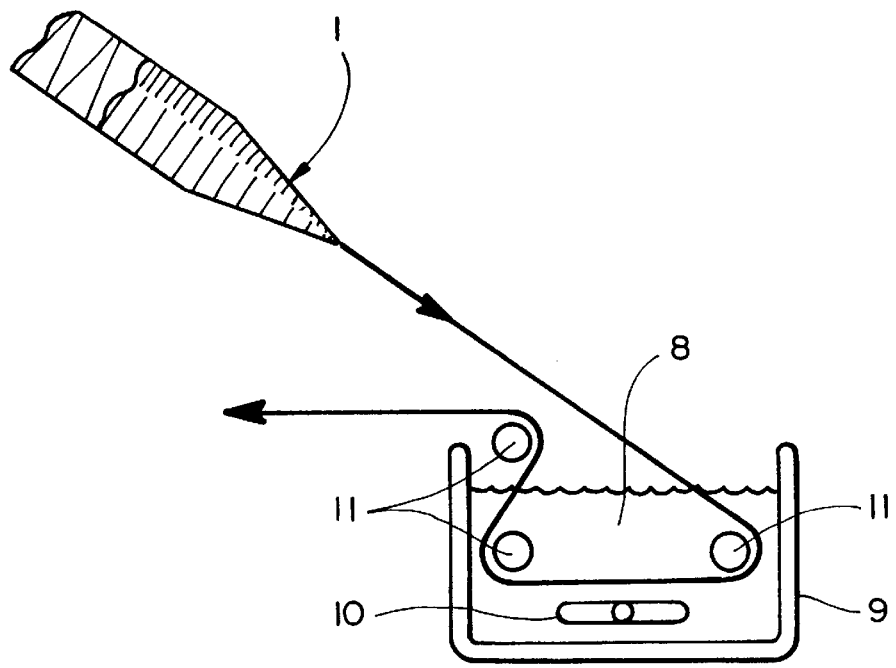
FIG_4A
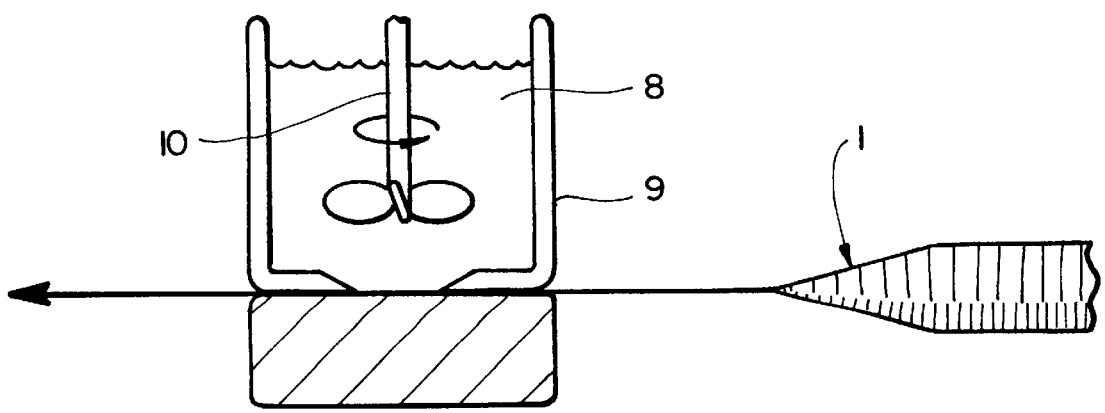
FIG_4B

OPAQUE REACTION MATRIX FOR THE ANALYSIS OF THE WHOLE BLOOD

This application is a continuation of Provisional Application 60/030,767, filed Nov. 8, 1996.

BACKGROUND OF THE INVENTION

1. Field of the Invention

The present invention relates to a system and method for determining the presence or concentration of analytes biological agents in a sample of bodily fluid, such as whole blood.

2. State of the Art

Currently membranes manufactured from various polymers, such as nylon, polysulfones, polyethyersulphones and polypropylene, are used in diagnostic applications to hold dry reagents, separate blood or create an absorbent pad to hold a sample. These membranes are made using various proprietary and patented techniques and each has specific properties useful to the diagnostic test for which they are used.

The market place for diagnostic systems is increasingly important and the ability to separate blood into relatively clear fluid and red blood cells is a critical factor in many tests. The tests are hindered by the fact that the membranes currently used become translucent when blood is applied and even when the red blood cells have been separated from the relatively clear fluid components, a shadow of the red blood cells is perceived by the spectrophotometric device used to read the test. At least two systems have attempted to compensate for the interference of red blood cells with the test reading. These systems include the Boehringer Mannheim "Accu-Chek Easy" and the LifeScan "SureStep" product. (See U.S. Design Pat. No. 367,109.) These test devices use multiple layers to separate and/or mask the interference of the red blood cells on the spectrophotometric reading taken by the test device reader. The types of materials used to separate red blood cells are fleece, glass fibers, absorbent pads and tight meshes of nylon, polypropylene or other polymers.

U.S. Pat. No. 4,340,479 describes a method for manufacturing a hydrophilic polyamide membrane. This membrane is used in U.S. Pat. No. 5,049,487 for a blood based test product which holds the reagents in a dry state prior to testing and provides a means of absorbing the blood sample during the test.

U.S. Pat. No. 5,186,843, Baumgardner et al., describes a cellulose and glass fiber material suitable for blood separation purposes.

U.S. Pat. No. 4,629,563, Wrasidlo, and U.S. Pat. No. 4,774,039, Wrasidlo, describe methods for manufacturing an asymmetric membrane which could be used to separate whole blood into relatively clear fluid and red blood cells. This type of material is referenced in U.S. Pat. No. 4,994,238, Daffern et al., and U.S. Pat. No. 4,774,192, Terminiello et al., to separate whole blood into relatively clear fluid and red blood cells.

U.S. Pat. No. 4,994,238, Daffem et al., teaches a device which uses an asymmetrically porous membrane having progressively finer filtration with increasing distance from the dosing surface. This patent further teaches an asymmetric membrane that provides a determined saturation volume and that provides progressively finer filtration which acts to filter cellular components of the sample at or near the sample receiving surface.

U.S. Pat. No. 4,774,192, Terminiello et al., teaches, for method of preparing a dry chemistry reagent system for detection and analysis of heterogeneous fluid samples. This patent also provides for a specific porous membrane of essentially uniform composition and a porosity gradient that extends from one surface to the opposite surface U.S. Pat. No. 5,456,835, Castino et al., teaches removing hemoglobin from blood by using a filter and hollow fiber or flat sheet of polyethersulfone. This system is used to filter out the leukocytes, hemoglobin and debris from blood.

U.S. Pat. Nos. 5,306,623 and 5,418,142, Kiser et al., teach a porous matrix with separation coating uniformly impregnated within. U.S. Pat. No. 5,418,142 more specifically defines the pore size. These patents teach that, as whole blood moves through the membrane, red blood cells encounter the separation component embedded in the matrix, whereby clear fluid passes through to the test side.

An object of the present invention is to improve the properties of transverse flow-through membranes for enzyme/substrate color development systems.

Another object of this invention is to provide a method for increasing the filtration performance of the membrane.

Yet another object of the invention is to provide a method to impregnate the membrane with fillers to block the interference of the red blood cells with the diagnostic reaction and the reading of the test indication.

Still another object of the invention is to provide an improved method for manufacturing test devices.

SUMMARY OF THE INVENTION

The present invention provides a method for preparing a reaction matrix system containing indicating reagents for the rapid analytical determination of substances in biological fluid samples which may contain cellular materials (such as erythrocytes) that can otherwise interfere with the determination. Using optical reflectance, a method is provided for masking and then monitoring the reactions of the resulting clear fluid. In a preferred embodiment the test device and a specific quantity of single use reagent bearing test chips are used to measure the concentration of glucose in whole blood. The present invention which can utilize existing or new membrane materials, involves adding a blocking filler to create an opaque membrane which can block interference of the red blood cells and/or can assist in the separation of red blood cells to provide relatively clear fluid for testing.

Accordingly, in one aspect, the present invention provides a test strip for use in determining the presence or concentration of an analyte in whole blood, said test strip comprising a porous membrane having disposed thereon (a) a separating agent capable of separating from whole blood, red blood cells and a fluid component substantially free of red blood cells; (b) an indicating reagent system capable of indicating the presence or concentration of an analyte in the fluid component by producing a spectrophotometric change upon contact with the fluid component; and (c) an opaque filler capable of reducing spectrophotometric interference caused by the presence of the red blood cells.

Preferably, the porous membrane employed in the test strip is selected from the group consisting of a polyethersulfone membrane, a polysulfone membrane and a nylon membrane. More preferably, the porous membrane is a polyethersulfone membrane.

Additionally, the porous membrane is preferably from about 0.002 to about 0.20 inches in thickness and has a mean pore size of about 0.1 to about 1 micron. In a preferred embodiment, the membrane is cast with a skin structure on one side and is isotropic through the remaining thickness of the membrane.

Preferably, the separating agent employed in the test strip is selected from the group consisting of polyvinyl sulfonic acid, polyethylene glycol, polystyrene sulfonic acid, hydroxypropyl cellulose, polyvinyl alcohol, polyvinylpyrrolidone, polyacrylic acid, citrates, formates, sulfates, amino acids, chitosan, citric acid, phytic acid, malic acid and mixtures thereof.

In one preferred embodiment, the separating agent is distributed homogeneously within the membrane. In another preferred embodiment, the separating agent is coated the surface of the membrane. In still another preferred embodiment, the separating agent forms an interior layer within the membrane.

Preferably, the opaque filler used in the test strip is selected from the group consisting of titanium dioxide, lime stone dust, plastic beads, talcum powder, calcium powder and mixtures thereof. More preferably, the opaque filler is titanium dioxide.

In one preferred embodiment, the opaque filler is distributed homogeneously within the membrane. In another preferred embodiment, the opaque filler is coated on the surface of the membrane. In still another preferred embodiment, the opaque filler forms an interior layer within the membrane.

Preferably, the indicating reagent system employed in the test strip comprises a glucose oxidase.

In another aspect, the present invention provides a method of testing whole blood for the presence or concentration of an analyte comprising:

(a) providing a test strip comprising a porous membrane having disposed thereon (i) a separating agent capable of separating from whole blood, red blood cells and a fluid component substantially free of red blood cells; (ii) an indicating reagent system capable of indicating the presence or concentration of an analyte in the fluid component by producing a spectrophotometric change upon contact with the fluid component; and (iii) an opaque filler capable of reducing spectrophotometric interference caused by the presence of the red blood cells;

(b) applying a whole blood sample to a first side of the test strip; and (c) reading or measuring on a second side of the test strip a spectrophotometric change in the fluid component.

In one preferred embodiment, the reading or measurement is provided by an instrument. In another preferred embodiment, the reading or measurement is provided visually.

BRIEF DESCRIPTION OF THE DRAWINGS

FIGS. 1A, 1B and 1C illustrate the distribution of particulate material in three membrane systems when applied to a uniform impregnation or to the precasting dope used to impregnate the membrane.

FIG. 2 illustrates membranes with uniformly changing pore size distribution (asymmetric, gradual gradient or anisotropic membranes) that can be dosed with a TiO$_2$ slurry such that the end result is a particulate zone.

FIGS. 3A and 3B illustrate membranes containing non-uniform pore size that can act as layering zones onto which an optical mask or barrier particles can be deposited. When this optical barrier is fixed to the matrix structure using film forming reagents, sample application to either surface is adaptable to pigment masking.

FIGS. 4A and 4B illustrate two methods of preparing particulate impregnated membranes.

DETAILED DESCRIPTION OF THE INVENTION

The objects, features and advantages of the present invention are realized by elimination or minimization of interference from red blood cell color when doing spectrophotometric or colorimetric testing.

The separation of red blood cells from whole blood is facilitated by the use of a porous membrane, such as a polyethersulfone membrane, which is cast with a skin structure on one side and isotropic through the remaining thickness of the membrane. The membrane specifications are from 0.002 to 0.20 inches in thickness and a mean pore size of between 0.1 to 1 micron.

The membrane is impregnated with separating agents which are fully described, for example, in U.S. patent application Ser. No. 08/628,489 and/or U.S. Pat. No. 5,306,623, Kiser et al., the disclosures of which are incorporated herein by reference. Suitable separating agents which can be applied to the membrane to increase its separation characteristics include, by way of example, polyvinyl sulfonic acid (PVSA); polyethylene glycol (PEG); polystyrene sulfonic acid (PSSA); hydroxypropyl cellulose (commercially available as Klucel™-EF); polyvinyl alcohol (PVA); polyvinylpyrrolidone (PVP); polyacrylic acid (PAA); water soluble salts; citrates; formates; sulfates; amino acids; chitosan (amino sugar); citric acid; phytic acid; malic acid; and mixtures thereof.

Preferably, the filler used in this invention is titanium dioxide. Other filler materials may be used to achieve similar results. Other materials which have been found to improve the blood separation and opacity are lime stone dust, plastic beads, talcum powder, calcium powder and the like. Generally, the maximum filler concentration employed in this invention is 25 weight percent.

The indicating reagent system used in this invention must be capable of detecting the presence of the analyte. In general, the analyte reacts with a specific oxidase enzyme and produces hydrogen peroxide. This strongly oxidative substance reacts with the indicator(s) present to produce a colored end product. The oxidase enzyme may be one of the following: glucose oxidase, cholesterol oxidase, uricase, alcohol oxidase, aldehyde oxidase or glycerophosphate oxidase. Other oxidase enzymes will be readily evident to one who is skilled in the art. The indicator chemistries which provide acceptable color generation when coated on the porous membrane may be chosen from 3-methyl-2-benzothiazolinone hydraaone hydrochloride (MBTH) combined with 3,3-dimethylaminobenzoic acid (DMAB), MBTH combined with 3,5-dichloro-2-hydroxybenzenesulfonic acid (DCHBS); 4-aminoantipyrene (4-AAP) (at 4 mg/mL) and 5-oxo-1-(p-sulfophenyl)-2-pyrazoline-3-arboxylic acid (OPSP); 4-AAP (at 4 mg/mL) and N-(m-tolyl)-diethanolamine (NDA); 2,2'-azino-di-(3-ethylbenzthiazoline)sulfonic acid (ABTS); 4-AAP (at 4 mg/mL) and 4-methoxynaphthol; pyrogallol red (PGR); bromopyrogallol red (BPR); acid green 25 (AG); MBTH and 8-anilino-1-naphthalenesulfonate (ANS); or N-(3-sulfopropyl)aniline and MBTH; or other known and conventional dye system for different analytes. U.S. Pat. No. 5,306,623 to Kiser et. al. discloses effective concentrations of a number of useful dye systems.

A preferred dye system is based on the sulfonated form of MBTH, 3-methyl-6-(M sulfonate)-benzothiazolinone-(2)- hydrazone (MBTH-S) where M is sodium, potassium, ammonium or other equivalent ion, but is preferably sodium. Sulfonation of MBTH to form MBTH-S is disclosed in U.S. Pat. No. 4,101,381 to Klose. MBTH-S formed as a dye couple with DMAB, ANS or N-(3-sulfopropyl)aniline provides preferred indicator systems having stable color end points in a short period of time.

The present invention improves the performance of the membrane and test strip by reducing the interference by the red blood cells and by contributing to the blood separation characteristics.

In a first preferred embodiment, a filler is used to increase the opaqueness of the membrane when a liquid sample, such as whole blood, is applied to it. In a preferred embodiment, the filler which is used is a fine sieve size titanium dioxide ($TiO_2$) powder. The material is mixed in the membrane polymer casting material and is cast as part of the membrane. The advantage to this is that the opacity of the membrane is increased and the irregular shape and weight of the $TiO_2$ particles create a boundary within the membrane which obstructs both red blood cell migration into the membrane and passage of light through the membrane.

Another preferred embodiment uses a filler, for example $TiO_2$, for impregnation into the membrane, which is then dried. The $TiO_2$ forms a interior layer within the membrane which both increases the opacity of the membrane and creates a layer of irregular shape interlocked members to help with the filtration to obstruct red blood cell migration. The $TiO_2$ is impregnated by mixing it with the various dips which are applied to the membrane or by a pretreatment application prior to adding the diagnostic mixtures.

In seeking an optically opaque reaction matrix, we unexpectedly found that membranes which separate cellular material from liquid components by means of a separation coating or by physical means can be made opaque to red pigmentation by adding $TiO_2$ to the separation coating or by adding $TiO_2$ to the coating dope prior to manufacturing of the membrane. FIGS. 1A–1C illustrate three types porous membranes 1 containing opaque filler particles 2: FIG. 1A illustrates a porous membrane having uniform pore size; FIG. 1B illustrates a porous membrane having varying pore size; and FIG. 1C illustrates a porous membrane having smaller pores on one side and larger pores on the opposite side. Preferred physical means separation membranes have a uniformly changing pore size distribution, such as the asymmetric, gradual gradient or anisotropic membranes shown in FIGS. 2 and 3. In FIG. 2, gradual shift in pore size distribution occurs internal to the porous membrane 1 going from one surface to the other. A separation coating excludes cells as they encounter reagent that is dissolving from the matrix walls. The $TiO_2$ contained in these structures forms a particulate zone 3 that masks the red pigmentation that is otherwise visible to the opposite surface. In seeking an optically opaque reaction matrix, we unexpectedly found that membranes containing non-uniform pore size distributions, in which a rapid shift in pore sizes occurs internal to the matrix, can act as layering zones onto which an optical mask or barrier can be placed using fluidics to deposit particles, such as $TiO_2$. When this optical barrier is fixed to the matrix structure using film forming polymers that do not readily dissolve in the presence of the fluid test sample, and when hydrophilic matrix supports containing pore sizes permissive to fluid transfer from one surface to the other are used, a highly adaptable matrix is constructed. Membranes of 0.2 $\mu$m skin side pore size, such as polyethersulfones from Gelman Sciences, are suitable for this application. To such a matrix, we have been able to optimize film forming coatings to make sample application to either surface adaptable to pigment masking when viewed from the opposite side for reading test results. For example, in FIG. 3, a whole blood sample 4 is applied to a porous membrane 1 having tight pore side 5, a particulate zone 6 comprising a opaque filler layer 3, and an open pore side. Regardless of the sequence of pore size change (open to closed or closed to open), when the particulate zone 6 is encountered, the pigmentation is not visible from the determining surface, i.e., the test indication side.

In a stirred coating trough, the dry membrane can be impregnation or coating on both sides by dipping (FIG. 4A) or can be wetted directly (FIG. 4B) to either surface for impregnation or coating without contact with the other surface. In FIG. 4A, the porous membrane 1 passes over rollers 11 through a coating trough 9 containing the slurry or liquid 8 which is stirred with stirrer 10. In FIG. 4B, the porous membrane 1 is coated on a single surface using a coating trough 9 containing the slurry or liquid 8 which is stirred with stirrer 10.

In providing optical opacity according to this invention, we also unexpectedly provided separation properties as well. Membrane systems where the cellular material of the test sample is not excluded at the receiving surface nor excluded by the "progressively finer filtration" internal to the matrix (as the pore size gradually decreases in size (porosity gradient) with increasing distance from the dosing surface toward the opposite surface) and membrane systems that are composed of non-uniform materials and in which a particulate zone exists internal to the matrix that acts to block opacity have the property of blocking red cells from penetration. The unique particulate zone functions both to block cellular penetration and to mask pigmentation in an otherwise translucent matrix. We have been able to optimize film forming coatings to make sample application to either surface adaptable to cellular exclusion at this zone. Regardless of the sequence of pore size change (open to closed or closed to open), when the particulate zone is encountered, cellular penetration to the determining surface does not occur. Additionally, a benefit to homogenous spreading of the sample has been noted when sample is applied to the more open pore sided matrix described. The particulate zone within the matrix in conjunction with the openness of this side of the matrix allows for free and fast absorption into the pores, followed by accelerated lateral flow due to the presence of the zone. The membrane therefore does not become saturated in a continuous manner. It is a three step process: 1) rapid porous side spreading, 2) quick lateral flow and slow penetration into the particulate zone and 3) slow but deliberate and homogenous penetration toward the determining surface.

The present invention provides, in one embodiment, a means of improving the filtration/separation of red blood cells from whole blood and it also increases the opacity of the membrane so that the red blood cell color transmission through the membrane is reduced. The next preferred embodiment is to mix the filler material into the casting dope of the membrane and increase the opacity by integrating it into the matrix. This also helps with blood separation due to the pore size modification that occurs within the substrate.

The present invention is further illustrated by the following examples.

EXAMPLE 1

Preparation of a Dip and a Coated Membrane $TiO_2$ is hydrated in a Standard Solution containing 7.45% Crotein and 0.5% Gantrez in 0.1 M Citrate at pH 7.0.

Thickening agents are required as described above and carboxy-methyl-ellulose (CMC) has been shown to be effective between 0.1 and 3.0%. The solution is degassed prior to further processing. The TiO$_2$ slurry is added at a concentration of 50 mg/mL.

In a stirred coating trough, the dry membrane to be impregnated is first allowed to contact the slurry only from the open pore side. This ensures that liquid is not saturating the inner pores of the membrane before the slurry containing the TiO$_2$ is allowed to enter the porous side and imbibe the membrane. This can be accomplished by using methods described in the attached drawings. In another embodiment the particulate slurry can be applied to the closed pore side. The film former will affix the particles to the surface. Full impregnation (FIG. 4A) or directed impregnation to either surface (FIG. 4B) are effective as described above.

EXAMPLE 2

Preparation of a Dope and a Homogeneous Membrane

A TiO$_2$ slurry is prepared in a similar method to that described in Example 1 above, but specifically for a casting process. TiO$_2$ is suspended in a polyethersulfone solution prepared as described in U.S. Pat. No. 4,900,449, Kraus et al., and degassed. The TiO$_2$ is added to a solids concentration that results in between 0.1 to 1.0 mg of TiO$_2$ per cm$^2$ of finished membrane.

EXAMPLE 3

Testing of a Coated Membrane

In this example, a coated membrane with TiO$_2$ prepared as described in Example 1 is compared to a control coated membrane with no TiO$_2$. The dips are structured to test the separation quality only and no reaction or indicator dye is added. Whole blood is spotted on one side of the membrane and the appearance of red on opposite side is noted and ranked for separation: no separation (red color and "0" separation), full separation (white color and "10" separation).

The control formulation contained the following:

20 mL water 120 mg citric acid(adjust pH to 4.2 with NaOH aqueous solution)

17 mg EDTA 95 mg Gantrz S95

240 mg Crotein SPA

The TiO$_2$ formulation contained the following:

20 mL water 120 mg citric acid(adjust pH to 4.2 with NaOH aqueous solution)

17 mg EDTA 95 mg Gantrz S95

240 mg Crotein SPA 1600 mg TiO$_2$

The results are shown in Table I below.

TABLE I

| TiO$_2$ Concentration: | 0.0 mg/mL | 2.5 mg/mL | 8.0 mg/mL | 25 mg/mL | 80 mg/mL |
|---|---|---|---|---|---|
| Ranked appearance on opposite side: | 1 | 3 | 5 | 7 | 9 |

The results in Table I show a marked reduction in the amount of red blood cell color being transmitted through the membranes containing TiO$_2$.

What is claimed is:

1. A test strip for use in determining the presence or concentration of an analyte in whole blood, said test strip comprising a porous membrane having disposed thereon (a) a separating agent capable of separating from whole blood, red blood cells and a fluid component substantially free of red blood cells; (b) an indicating reagent system capable of indicating the presence or concentration of an analyte in the fluid component by producing a spectrophotometric change upon contact with the fluid component, said indicating reagent system comprising 3-methyl-6-(M sulfonate)-benzothiazolinone-(2)-hydrazone, where M is sodium, potassium or ammonium; and (c) an opaque filler capable of reducing spectrophotometric interference caused by the presence of the red blood cells.

2. The test strip of claim 1 wherein the porous membrane is selected from the group consisting of a polyethersulfone membrane, a polysulfone membrane and a nylon membrane.

3. The test strip of claim 1 wherein the porous membrane is a polyethersulfone membrane.

4. The test strip of claim 2 wherein the membrane is from about 0.002 to about 0.20 inches in thickness and has a mean pore size of about 0.1 to about 1 micron.

5. The test strip of claim 4 wherein the membrane is cast with a skin structure on one side and is isotropic through the remaining thickness of the membrane.

6. The test strip of claim 1 wherein the separating agent is selected from the group consisting of polyvinyl sulfonic acid, polyethylene glycol, polystyrene sulfonic acid, hydroxypropyl cellulose, polyvinyl alcohol, polyvinylpyrrolidone, polyacrylic acid, citrates, formates, sulfates, amino acids, chitosan, citric acid, phytic acid, malic acid and mixtures thereof.

7. The test strip of claim 6 wherein the separating agent is distributed homogeneously within the membrane.

8. The test strip of claim 6 wherein the separating agent is coated on the surface of the membrane.

9. The test strip of claim 6 wherein the separating agent forms an interior layer within the membrane.

10. The test strip of claim 1 wherein the opaque finer is selected from the group consisting of titanium dioxide, lime stone dust, plastic beads, talcum powder, calcium powder and mixtures thereof.

11. The test strip of claim 10 wherein the opaque filer is titanium dioxide.

12. The test strip of claim 10 wherein the opaque filler is distributed homogeneously within the membrane.

13. The test strip of claim 10 wherein the opaque filler is coated on the surface of the membrane.

14. The test strip of claim 10 wherein the opaque filler forms an interior layer within the membrane.

15. The test strip of claim 1 wherein the indicating reagent system comprises a glucose oxidase.

16. A method of testing whole blood for the presence or concentration of an analyte comprising:

(a) providing a test strip comprising a porous membrane having disposed thereon (i) a separating agent capable of separating from whole blood, red blood cells and a fluid component substantially free of red blood cells; (ii) an indicating reagent system capable of indicating the presence or concentration of an analyte in the fluid component by producing a spectrophotometric change upon contact with the fluid component, said indicating reagent system comprising 3-methyl-6-(M sulfonate)-benzothiazolinone-(2)-hydrazone, where M is sodium, potassium or ammonium; and (iii) an opaque filler capable of reducing spectrophotometric interference caused by the presence of the red blood cells;

(b) applying a whole blood sample to a first side of the test strip; and (c) reading or measuring on a second side of the test strip a spectrophotometric change in the fluid component to determine the presence or concentration of the analyte.

17. The method of claim 1 wherein the reading or measurement is provided by an instrument.

18. The method of claim 1 wherein the reading or measurement is provided visually.

19. The method of claim 1 wherein the porous membrane is selected from the group consisting of a polyethersulfone membrane, a polysulfone membrane and a nylon membrane.

20. The method of claim 19 wherein the porous membrane is a polyethersulfone membrane.

21. The method of claim 19 wherein the membrane is from about 0.002 to about 0.20 inches in thickness and has a mean pore size of about 0.1 to about 1 micron.

22. The method of claim 21 wherein the membrane is cast with a skin structure on one side and is isotropic through the remaining thickness of the membrane.

23. The method of claim 16 wherein the separating agent is selected from the group consisting of polyvinyl sulfonic acid, polyethylene glycol, polystyrene sulfonic acid, hydroxypropyl cellulose, polyvinyl alcohol, polyvinylpyrrolidone, polyacrylic acid, citrates, formates, sulfates, amino acids, chitosan, citric acid, phytic acid, malic acid and mixtures thereof.

24. The method of claim 23 wherein the separating agent is distributed homogeneously within the membrane.

25. The method of claim 23 wherein the separating agent is coated on the surface of the membrane.

26. The method of claim 23 wherein the separating agent forms an interior layer within the membrane.

27. The method of claim 16 wherein the opaque filler is selected from the group consisting of titanium dioxide, lime stone dust, plastic beads, talcum powder, calcium powder and mixtures thereof.

28. The method of claim 27 wherein the opaque filler is titanium dioxide.

29. The method of claim 27 wherein the opaque filler is distributed homogeneously within the membrane.

30. The method of claim 27 wherein the opaque filler is coated on the surface of the membrane.

31. The method of claim 27 wherein the opaque filler forms an interior layer within the membrane.

32. The method of claim 16 wherein the indicating reagent system comprises a glucose oxidase.

* * * * *